(12) United States Patent
Mian et al.

(10) Patent No.: US 11,961,232 B2
(45) Date of Patent: Apr. 16, 2024

(54) AUTOMATED SENSING SYSTEM FOR HEALTH DETECTION

(71) Applicants: Zahid F. Mian, Loudonville, NY (US); Noreen F. Mian, Loudonville, NY (US)

(72) Inventors: Zahid F. Mian, Loudonville, NY (US); Noreen F. Mian, Loudonville, NY (US)

(73) Assignee: International Electronic Machines Corp., Troy, NY (US)

( * ) Notice: Subject to any disclaimer, the term of this patent is extended or adjusted under 35 U.S.C. 154(b) by 71 days.

(21) Appl. No.: 17/375,104

(22) Filed: Jul. 14, 2021

(65) Prior Publication Data

US 2022/0020149 A1 Jan. 20, 2022

Related U.S. Application Data

(60) Provisional application No. 63/052,090, filed on Jul. 15, 2020.

(51) Int. Cl.
| | |
|---|---|
| *H04N 5/33* | (2023.01) |
| *G01J 5/00* | (2022.01) |
| *G06T 7/00* | (2017.01) |
| *G06V 20/52* | (2022.01) |
| *G06V 40/16* | (2022.01) |

(52) U.S. Cl.
CPC .......... *G06T 7/0012* (2013.01); *G01J 5/0025* (2013.01); *G06V 20/53* (2022.01); *G06V 40/161* (2022.01); *G06V 40/171* (2022.01); *H04N 5/33* (2013.01); *G01J 2005/0077* (2013.01)

(58) Field of Classification Search
CPC ....... A61B 5/0075; A61B 5/0077; A61B 5/01; A61B 5/02055; A61B 5/1128; A61B 5/746

See application file for complete search history.

(56) References Cited

U.S. PATENT DOCUMENTS

| | | | | |
|---|---|---|---|---|
| 2005/0234742 | A1* | 10/2005 | Hodgdon | G06Q 10/10 705/2 |
| 2010/0100275 | A1* | 4/2010 | Mian | G01M 17/013 382/284 |
| 2010/0161255 | A1* | 6/2010 | Mian | G01N 29/4463 702/56 |
| 2013/0072807 | A1* | 3/2013 | Tran | A61B 5/4833 600/595 |
| 2014/0339374 | A1* | 11/2014 | Mian | G08G 1/04 246/473.1 |
| 2019/0105006 | A1* | 4/2019 | Mian | G06T 5/50 |
| 2020/0297206 | A1* | 9/2020 | Zakharov | A61B 5/6803 |
| 2020/0345274 | A1* | 11/2020 | Ghoshal | A61B 5/1135 |
| 2020/0388403 | A1* | 12/2020 | Boulos | G06F 21/57 |

* cited by examiner

*Primary Examiner* — Md N Haque
(74) *Attorney, Agent, or Firm* — LaBatt, LLC (57) ABSTRACT

A system and method for detecting medical conditions in individuals in crowded settings is described, including methods and approaches for addressing confounding issues such as variation due to external factors.

20 Claims, 11 Drawing Sheets

Preferred Embodiment Illustration

AUTOMATED SENSING SYSTEM FOR HEALTH DETECTION

REFERENCE TO RELATED APPLICATIONS

The current application claims the benefit of U.S. Provisional Application No. 63/052,090, filed on 15 Jul. 2020, which is hereby incorporated by reference herein.

TECHNICAL FIELD

The disclosure relates generally to the detection and evaluation of the health conditions of human subjects in an area.

BACKGROUND OF THE INVENTION

Human based, manual measurements of an individual or groups health attributes are not practical for large-scale monitoring of areas (train or airport terminals, shopping malls, etc.) due to the cost—in time, money, and personnel—to examine every person entering the area. Automated remote measurement appears to be the only practical approach to performing such evaluation in large-scale, well-populated areas. However, capturing automated measurement by taking facial temperature is inaccurate, for a number of reasons that may be dependent on external conditions (temperature, humidity, sunlight, etc.) or on the sensing technology (variations in the emissivity of skin causing variations in assessed temperature, for example). Accurate temperature can be obtained only by capturing temperature of certain areas around the eye, i.e. tear duct area (specifically the inner canthus), or by careful compensation for the various factors which lead to inaccurate readings from other areas of the face. While locating a human face in a crowded scene is a technique well-known to those skilled in the art, locating specific areas on a human face is not, especially in a low resolution thermal image. Even in a high resolution thermal image, the feature extraction can be quite complicated due to poor contrast in thermal images. The present invention offers a unique method to capture accurate human temperature by segmenting a crowded natural scene, locating key thermal temperature areas on the human face, and then processing the extracted image for accurate human body temperature.

Many conventional means for assessing "core temperature" (the temperature maintained at the essential "core" areas of the body, such as heart, brain, lungs) are impractical to use in an automated monitoring setup; ear (tympanic) infrared thermometers, forehead (temporal artery) and stick thermometers (oral, rectal, armpit) require direct and precise positioning on the body and are in many cases intrusive. Correct and timely placement of these types of thermometers is beyond the capabilities of today's autonomous robots, and is physically impractical in large-group locations such as those specified earlier. It follows that a practical automated body temperature measurement system must be based on remote temperature sensing.

SUMMARY OF THE INVENTION

The invention described is intended to overcome the limitations of current art methods of detecting the health of one or more people in locations of interest. This information is to be automatically conveyed to a remote monitor. Current art requires human operated stations to either measure body temperature with contact sensors or thermal sensors with limited precision and accuracy, and no consideration for contributing factors that influence translation of sensor measurements to core body temperature, or the use of other methods of health assessment beyond temperature.

In one preferred embodiment, imagery is acquired from co-located and co-registered infrared and visible light cameras. Automated algorithms are applied to this fused imagery to identify and locate all individuals, further identify and locate body features of interest from each individual, acquire thermal readings from these body features and convert from thermal sensor outputs to individual-specific core body temperature. Acoustic and/or other sensors are used to detect sounds or movements such as coughing or sneezing which may also indicate health issues. A detection of significant abnormality in any of these indicators will result in an alert indicating special follow-up procedures to be executed. Other embodiments of various devices and systems related to this basic concept are also described.

In the preferred embodiment, the infrared camera is combined with simple processing electronics and integrated into an automated system to obtain accurate data on temperature and other characteristics from infrared images of the eye and equipped with wired or wireless communication means to transfer this data to a more capable local device which may carry out assessment on the data and further transmit this data to a remote location and notify the local user as well if a condition of concern exists; this device is a part of a system which may incorporate numerous other sensors and which all communicate to the more capable local device. Other embodiments of various devices and systems related to this basic concept are also described.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

DETAILED DESCRIPTION OF THE INVENTION

Figure 1:
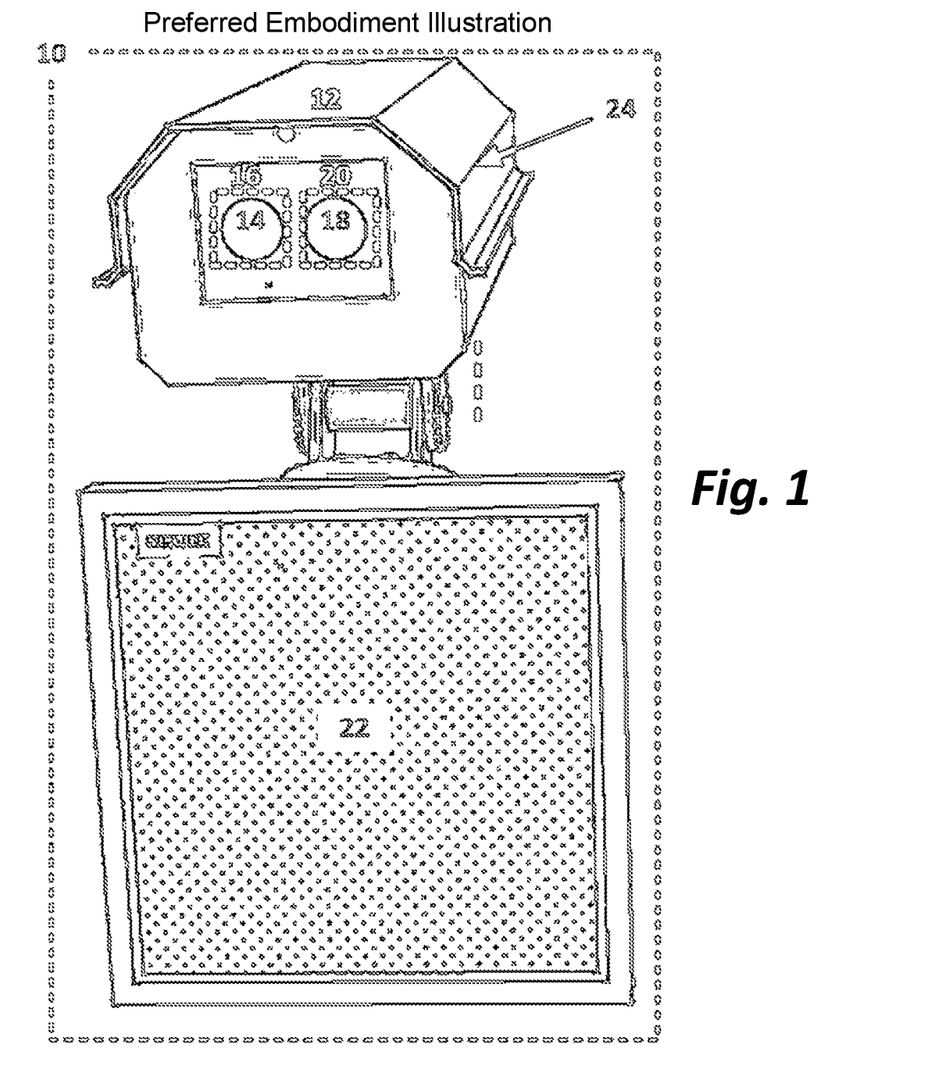
FIG. 1 illustrates a preferred physical embodiment of the invention.

In FIG. 1, the invention 10 includes an enclosure 12, which protects the other components of the invention from the environment; an IP66 closure would be a likely rating, proof against most forms of weather and sealed against dust intrusion. Within enclosure 12, there is a first camera 14 sensitive to a wavelength band (band-1), and which may be provided with a scene illuminator for that wavelength band 16. Also, there is a second camera 18 sensitive to another wavelength band (band-2), and this camera 18 may also be provided with a scene illuminator for that wavelength band 20. In other embodiments, more cameras may be added for various bands, and may or may not require illuminators.

In any event, the preferred embodiment is also equipped with an acoustic microphone array 22 which provides directional sound reception. This may be through beam-steering, through an adjustable parabolic microphone, or by any other means known to those skilled in the art. Within the enclosure 12 there are also processing electronics 24 which collect data from the sensors 14, 18, 22, analyze them according to procedures detailed later, and may transmit data as required.

It is assumed that the preferred embodiment is connected via wires or cables to both power and data/control systems, but this should not be construed to say or imply that the present invention could not be made to be wireless and self-powered, say by adding solar panels or other power sources known to those skilled in the art.

In the preferred embodiment, first camera 14 is a visible light imaging camera and second camera 18 is a thermal imaging camera in the LWIR or MWIR bands.

Figure 2:
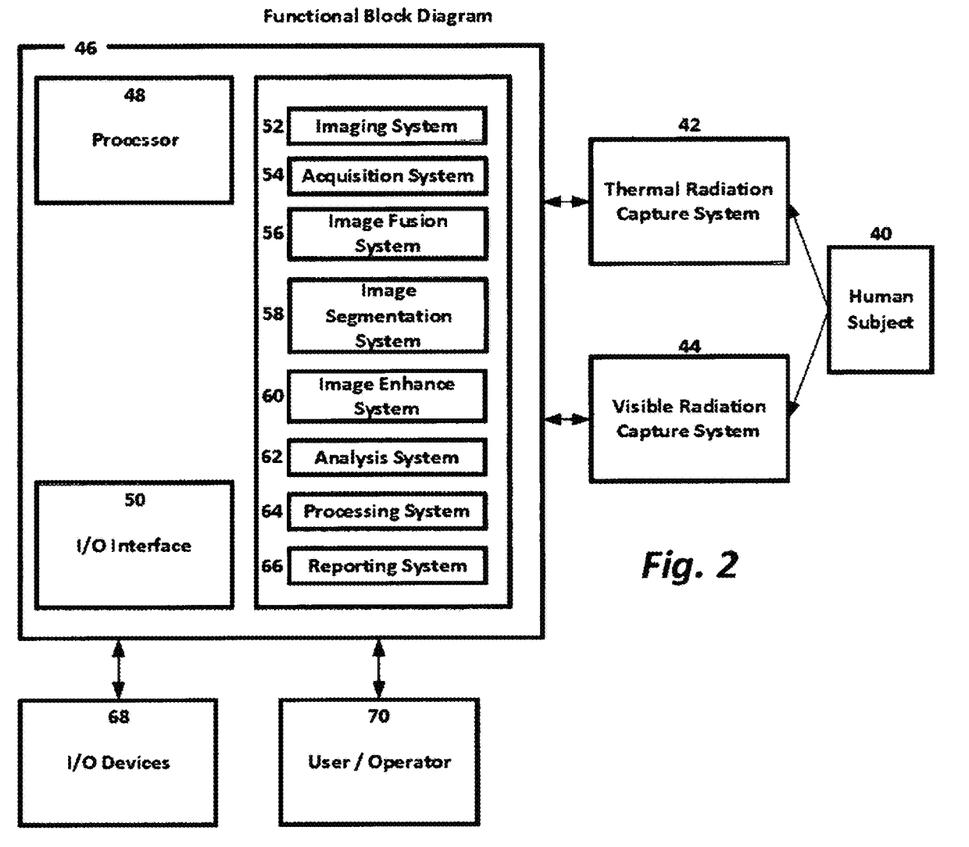
FIG. 2 illustrates a functional block diagram of the preferred embodiment.

In any event, the proposed embodiment also includes a process system to achieve the described goals, shown in FIG. 2. A human subject or subjects 40 are imaged both by a thermal radiation capture system 42 and a visible radiation capture system 44. These systems 42 and 44 are connected to the main processing system 46, which includes a processor 48 (which may be a single processor or multiple processors in actual practice, as known to those skilled in the art of microprocessing systems) and an I/O (input-output) interface 50. Within the processing system are also included multiple subsystems, some purely software, others including more or less hardware. These include the imaging system 52, which includes the previously described cameras 14 and 18 and their electronics; the data acquisition system 54, which accepts the data from the imaging system 52 and sends it to the image fusion system 56; this fusion system 56 performs the final co-registration operations on the images, allowing key analysis to be performed on both sensing modalities with respect to the other modality.

The image segmentation system 58 locates and extracts the key features in either or both image sets, which includes detecting and defining individual human subjects and, later, individual features of each subject, while the image enhancement system 60 performs various operations that may improve the quality and usability of captured images. This may include deblurring algorithms, or if multiple frames of video are available super-resolution algorithms may be used, or any other image enhancement processes known to those skilled in the art.

Following this preliminary processing, an image analysis 62 is performed to determine various conditions or parameters of interest. These are processed 64 to arrive at a decision as to a need for any action to be performed, and then passed to a reporting system 66 which transmits the information out of the main processing system 46 as needed.

Such information from the reporting system 66 may be transmitted to various I/O devices 68, or to a user/operator 70. It is possible for the user/operator 70 or I/O devices 68 to also direct actions or modify parameters of any of the subsystems within system 46 under appropriate circumstances.

Figure 3:
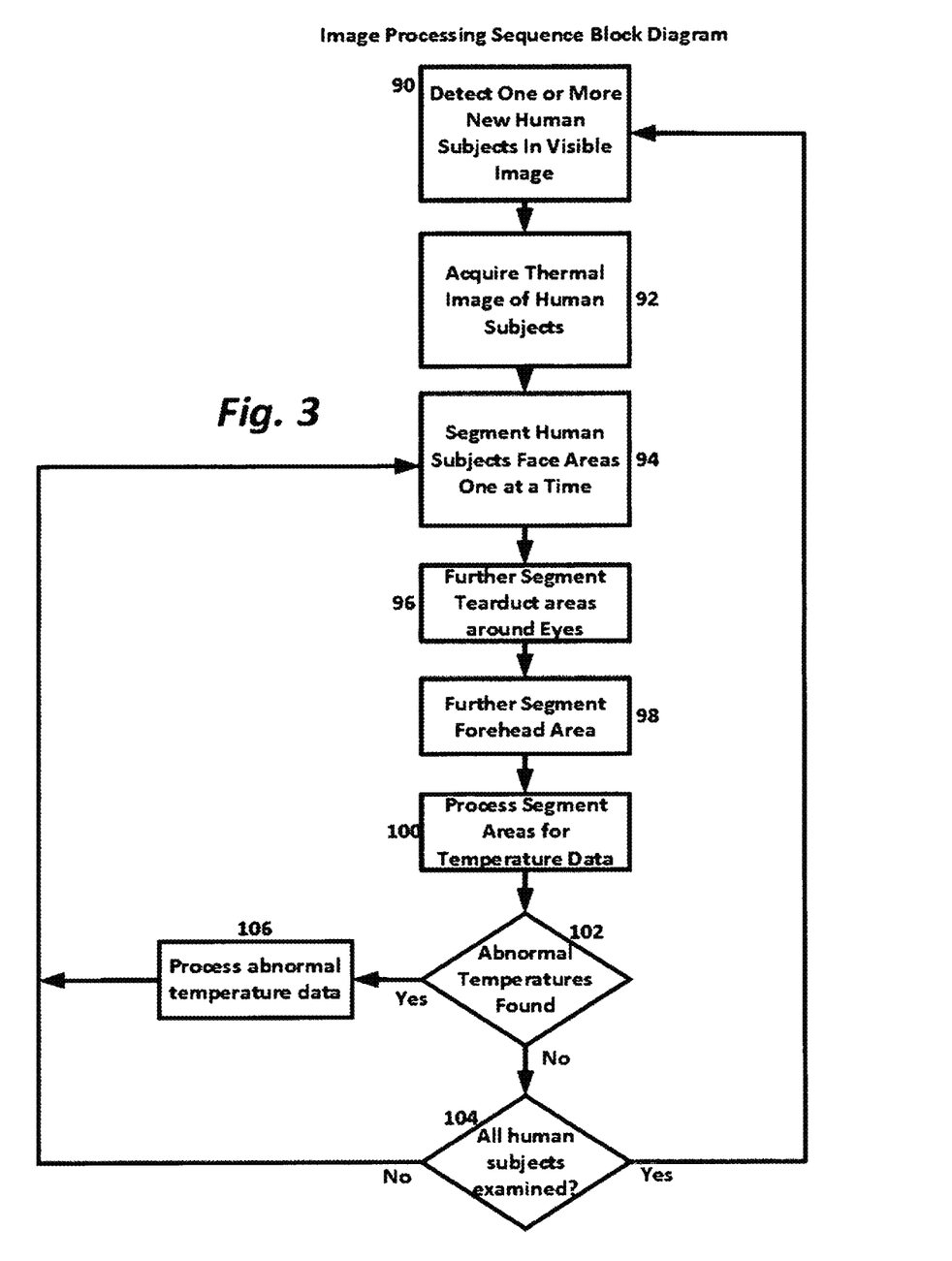
FIG. 3 is a diagram illustrating the basic image processing concepts of the invention.

To achieve the goals of the invention, images are processed according to an approach described generally in FIG. 3. The invention detects 90 one or more new (not previously processed) human subjects in the visible light image. The thermal camera acquires images 92 of these human subjects, and then performs the following sequence of operations on each subject in order.

First, the subject's face is segmented 94 to locate the major key features of interest (forehead, eyes, nose, etc.); with these key locations known, additional segmentation is performed to localize the tearduct and eye areas 96. The forehead area is also further segmented 98 to allow multiple evaluations across this broader area. The selected segmented areas are processed 100 for temperature data. If no abnormal temperatures are noted 102, the system checks 104 to see if all known human subjects have been evaluated; if they have been, the system returns to 90, otherwise the system continues to process the next face at 94. If abnormal temperatures are seen, the system evaluates the abnormal temperature data 106, and then continues to process the remaining faces 94.

It is well-known that emissivity varies based on the nature and composition of a target; in the case of human skin, it is known to vary based on fat content, humidity, temperature, and other factors, although most of these variations are relatively small. This is much less true for variations caused by cosmetics, as these may directly change infrared emissivity by changing the physical composition of the surface of the skin. Even materials that do not affect skin color in visible light can cause drastic changes in apparent emissivity/color in other spectra; an extreme version of this is sunscreen, which can be invisible in regular light but which makes human skin far more reflective (as well as absorptive) in ultraviolet light.

Figure 4A:
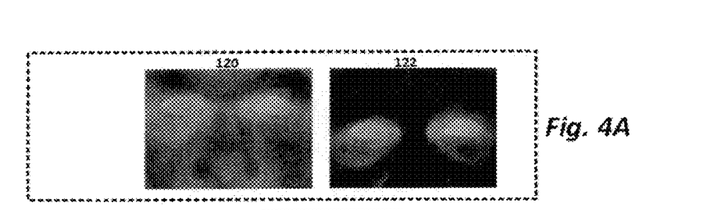
FIG. 4A shows an example of infrared facial variation from externally-applied sources

There is an associated challenge based on very recently applied cosmetics and other instances in which something may have been applied to the face that changes its temperature, such as cold water (rain, snow, etc.). These may be detected through the examination of the precise pattern of temperatures seen across images; the human face has well-established heat patterns which will be disrupted by any general application of a substance of a different temperature or inherent emissivity in the infrared. FIG. 4 illustrates an example of this phenomenon and outlines a procedure to address these issues. In FIG. 4A, there is an image of part of a human face 120, and an image of the same face following immersion in cold water 122. It can be seen that the major difference between these areas is a reduction in temperature of all areas which has rendered them nearly uniform in temperature, except for the eyes and their immediate surroundings. This suggests two possible metrics for distinguishing between a face of normal temperature distribution and one with an abnormal temperature distribution: the first is a general histogram of temperature distributions across the face, which will vary significantly from the norm if any large area of the face has its temperature distribution shifted, and the second is to compare contrast ratios between key elements of the face, such as the eyes, nose, cheeks, and forehead. As the eyes tend to maintain their temperature, the contrast between the eyes and other areas of the face will vary significantly if the temperature distribution shifts.

Similar procedures may be used for differentiating between a face untreated with interfering cosmetics, creams, or other materials and one that has been; it would be extremely difficult to apply such a material in a manner that would reduce the apparent temperature of the face without interfering in the common heat patterns of the face, and thus a knowledge of the appropriate contrast ratios, histograms, or other metrics would allow the detection of the existence of materials that may be biasing the apparent temperature measurement. These procedures may also detect wearers of particular types of contact lenses if resolution is sufficient.

If a specific pattern of application and temperature variation can be distinguished, it may also be possible to perform compensation for these variations. For example, if it is known that a given cosmetic application results in a reduction of one degree in the measured temperature, measured temperatures in the areas covered by the cosmetic may be adjusted upward by one degree to compensate. In general, it would be preferable to focus on the area of the eyes, such as the tearducts, which are likely to be unaffected by such exterior applications.

Figure 4B:
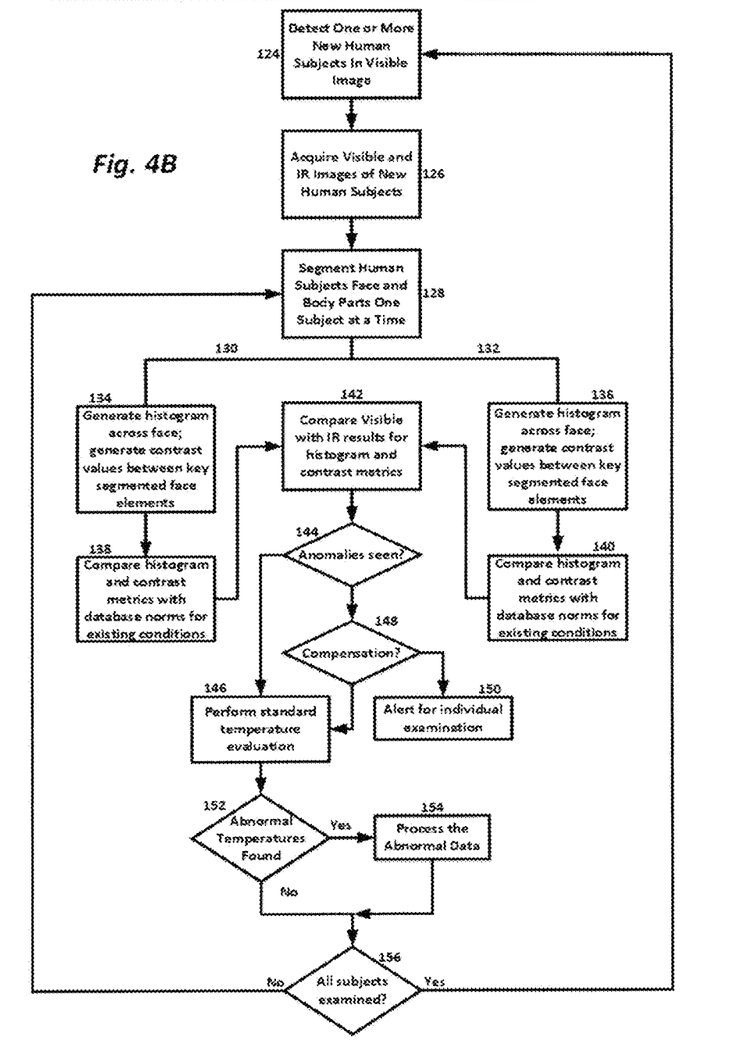
FIG. 4B is a flowchart of a method to detect and address infrared variation from externally supplied sources

FIG. 4B illustrates this process as a subroutine that could function as a supplement to or expansion of the processes in FIG. 3. New human subjects are detected 124 in the visible imagery, which triggers the acquisition 126 of both visible and infrared images of the new subjects. Each human subject image is segmented 128 into key face and body elements, which are then analyzed in both visible 130 and infrared 132 paths. Histograms across the face and contrast metrics between key face/body elements are determined for both visible 134 and infrared 136, and then are compared with database norms for visible 138 and infrared 140; the visible and infrared results are compared 142 to further detect additional anomalies based on the separate results; this is a form of sensor fusion. If no anomalies 144 are seen, the standard temperature evaluation 146 is performed; if anomalies 144 are seen, they are examined to see if compensation 148 is feasible by known means. If compensation is feasible it is performed and standard temperature evaluation 146 follows. If no compensation is feasible, the individual is flagged with an alert 150 for individual examination.

Following temperature evaluation, if abnormal temperatures are found 152, the abnormal data is processed 154; following this, or if no abnormal temperatures 152 are found, the system checks to see if all subjects have been examined 156; if not, the system returns to continue segmentation of subjects 128, otherwise the system returns to detecting new subjects 124.

Figure 5:
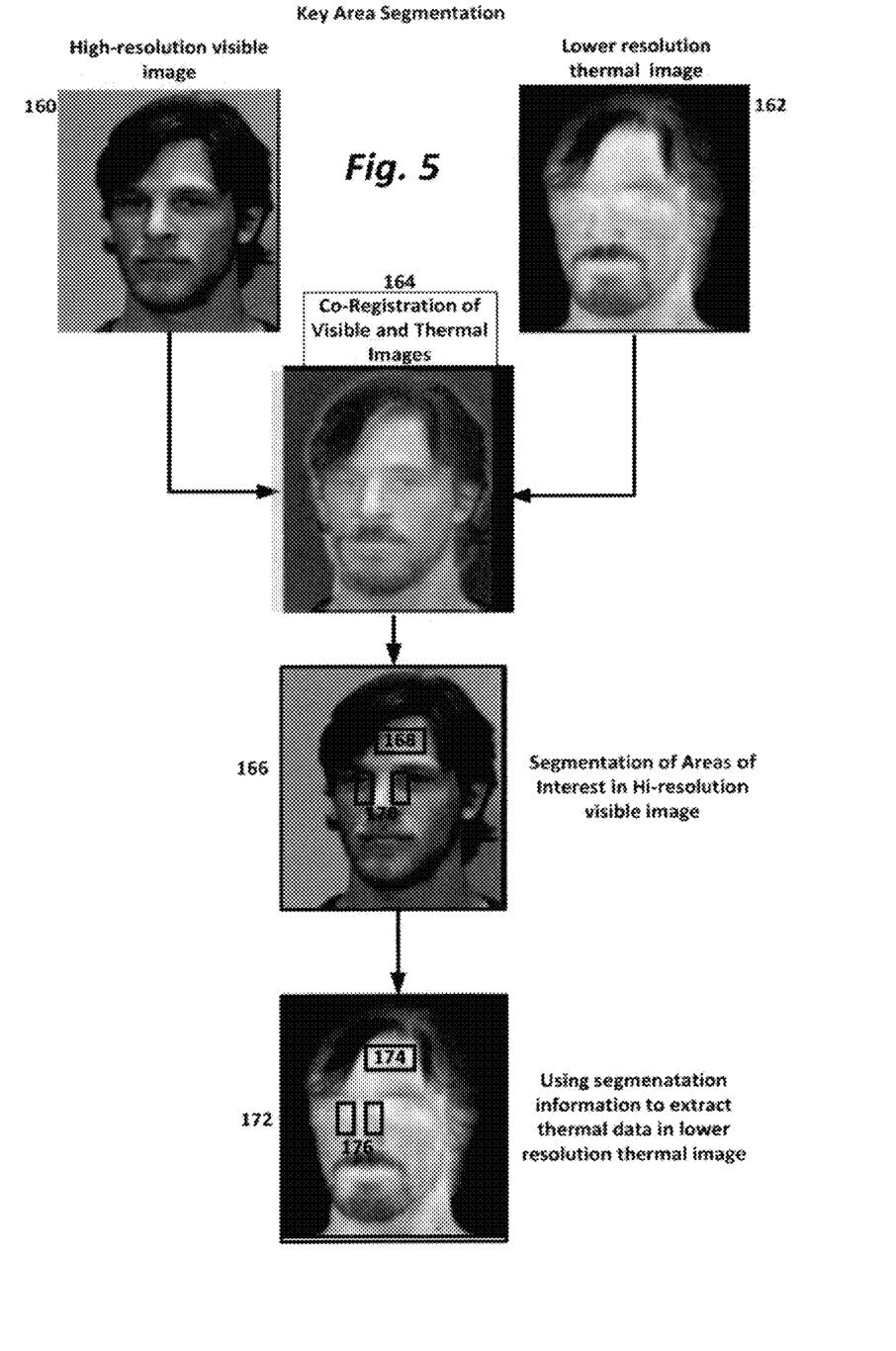
FIG. 5 illustrates the use of both visible light and thermal imaging to segment and recognize key areas of an individual face

The segmentation of key areas from an image is obviously an important component of the present invention. In addition, the use of both visible and thermal imaging is also key. FIG. 5 illustrates the basic process that permits a useful segmentation and examination of these images in two different spectra. In FIG. 5, a high resolution visible-light image 160 is acquired, along with a lower-resolution thermal infrared image 162. The lower resolution of the thermal image is a general assumption based on the current and past state of imaging technologies, in which much higher resolution images can be obtained in visible light by relatively low-cost cameras, while even quite expensive thermal infrared cameras; for example, as of this writing the highest resolution, easily commercially available visible-light video cameras are 8192×4320 pixels or 35 megapixels in resolution, while the highest resolution thermal IR cameras reach 1920×1200 pixels or 2.3 megapixels. The present invention does not, however, exclude the possibility of using a visible light camera and a thermal camera of any resolution that provides sufficiently clear imagery.

In any event, the cameras 14 and 18 (from FIG. 1) which provide the images 160 and 162 are aligned and provided with optics such that their fields of view are as coincident as may be practical. This and additional calibration and proper calculations allow the two images 160 and 162 to be co-registered 164; that is, there is a direct and known correspondence of features and locations in one image to features and locations in the other.

The assumed higher-resolution image 160 is then processed by any means known to those skilled in the art of image analysis to produce a segmentation 166 of the image to locate key areas of interest in the image; in the case of FIG. 5 these key areas are assumed to be the forehead 168 and the areas around the tear ducts 170.

The tear ducts are specifically targeted because the area of the eye near them—specifically, the inner canthus—has been shown to be an excellent indicator of core temperature, rivalling the ear tympani and possibly better than the eyeball itself due to being better protected.

Using the co-registration 164, the thermal image 162 is segmented 172, into areas corresponding to the thermal image of the forehead 174 and the thermal image of the tearduct and canthus region 176. From these, measurements of body temperature may be extracted as described in prior figures.

In a real-world setting, there are various conditions which may interfere in the acquisition of temperature as described. For example, a subject may be wearing a hat or scarf which partially or completely obscures the forehead, or wearing glasses; while visible light can penetrate glasses, thermal infrared cannot, and thus glasses would preclude any chance of properly imaging the target eye areas. In theory, any area of exposed skin could serve for temperature measurement, although with increasing uncertainty. The system must be able to address any possible combination of measurement situations.

Figure 6:
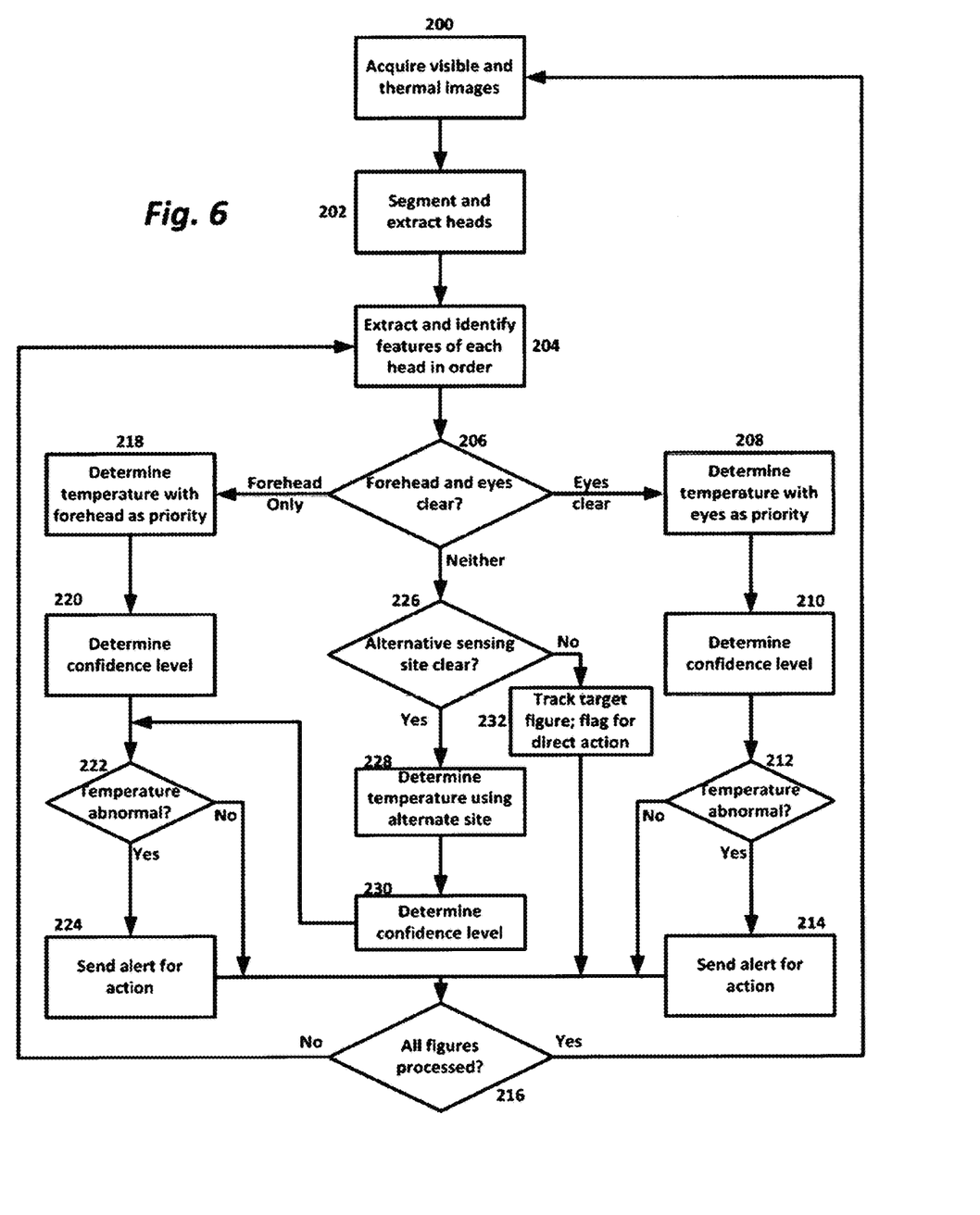
FIG. 6 illustrates a choice methodology for determining which segmented targets to use for temperature measurement

FIG. 6 describes such a process, which may be considered to be a subprocess of or overlay/addition to some of the previously presented figures such as FIGS. 3 and 4. Visible and thermal images are acquired 200, and segmented 202 to extract the head and possibly other body components from each human figure. Features of each head are then extracted 204 in order (so that all figures will be addressed). Once the various features are extracted 204, they are evaluated 206 by image processing methods to determine whether the forehead and/or eyes are unobstructed sufficiently to permit effective use of these areas for temperature measurement. If the eyes or both the eyes and the forehead are unobstructed, the eyes are the primary choice for temperature determination 208; a confidence level is assigned 210 to the temperature measured (generally very high with the eye measurement, moderate with forehead, generally lower with other target areas such as hands or arms). If an abnormal temperature is detected 212, an appropriate alert for action is given 214; following this, or if no abnormal temperature was detected, the system checks 216 to see if all figures have been processed; if they have not, the system returns to the extraction of features 204; if they have, it returns to the acquisition of new images 200. Note that for this and following paragraphs of the description, different types or levels of alert may be given depending on the exact measured temperature and the confidence level assigned to that temperature.

If only the forehead is clear for measurement, it becomes the subject of temperature determination 218. A confidence level is assigned 220 to this temperature, and if the temperature is abnormal 222 an alert is sent 224; subsequent to alert or a normal temperature reading, the system returns to evaluate the state of figure processing 216.

If neither the forehead nor the eyes are clear, alternative sensing sites are examined 226. If any of these are clear, temperature is evaluated 228 based on the selected alternative site; there may be multiple alternative sites and if so they would be examined in order to use the best-ranked site available. Following temperature measurement, the measurement would be assigned a confidence interval 230. If the temperature was abnormal 222, an alert would be sent 224. Following this, or if the temperature was not abnormal, the system would return to evaluate the state of figure processing 216.

If no alternative sensing sites are clear for measurement, the target will be tracked and flagged for direct action (examination by qualified personnel) 232. Following this, the system returns to evaluate the state of figure processing 216. Such flagging could also occur if the assigned confidence level falls below some determined value, or under other combinations of circumstances that will be obvious to those skilled in the art.

As a general example, as the eye-based measurements are expected to have high confidence values, a measurement of a temperature significantly above normal (for example, 100 degrees F.) would automatically generate an alert of fever. For an area with low confidence values (for example, the arms), it might be that a considerably greater departure from expected temperatures, such as 102 degrees F. (adjusted for known conditions, such as outside temperature, precipitation, etc.) would be required to trigger a fever alert. Alternatively, individuals presenting no high-confidence areas could be automatically marked for personal screening, where this would be practical.

It is well known that the accuracy of temperature measurement varies both with the accuracy of the sensor and with various other factors such as the temperature of the environment. The imaging sensors of the cameras 14 and 18 may be directly calibrated by imaging a known target of controlled temperature, and constructing from this image a pixel-by-pixel offset calibration matrix which when applied causes all of the pixels to report the same temperature. To ensure that this offset calibration is valid across key temperature ranges, multiple calibration matrices may be calculated for multiple temperatures and calibration curves related to the temperatures be determined. As the preferred embodiment of the invention is to be used in indoor settings, the two temperature ranges of interest are those of standard indoor settings (between, for example, 65 and 85 degrees F.) and the actual temperature range of the human body (~94 to 106 degrees F.).

Even with a clear calibration function usable across the key temperature ranges for the individual sensors, the readings returned from thermal imaging cameras are still affected by external factors, including temperature and humidity. Thus, the preferred overall system embodiment includes devices and methods to address these challenges.

Figure 7:
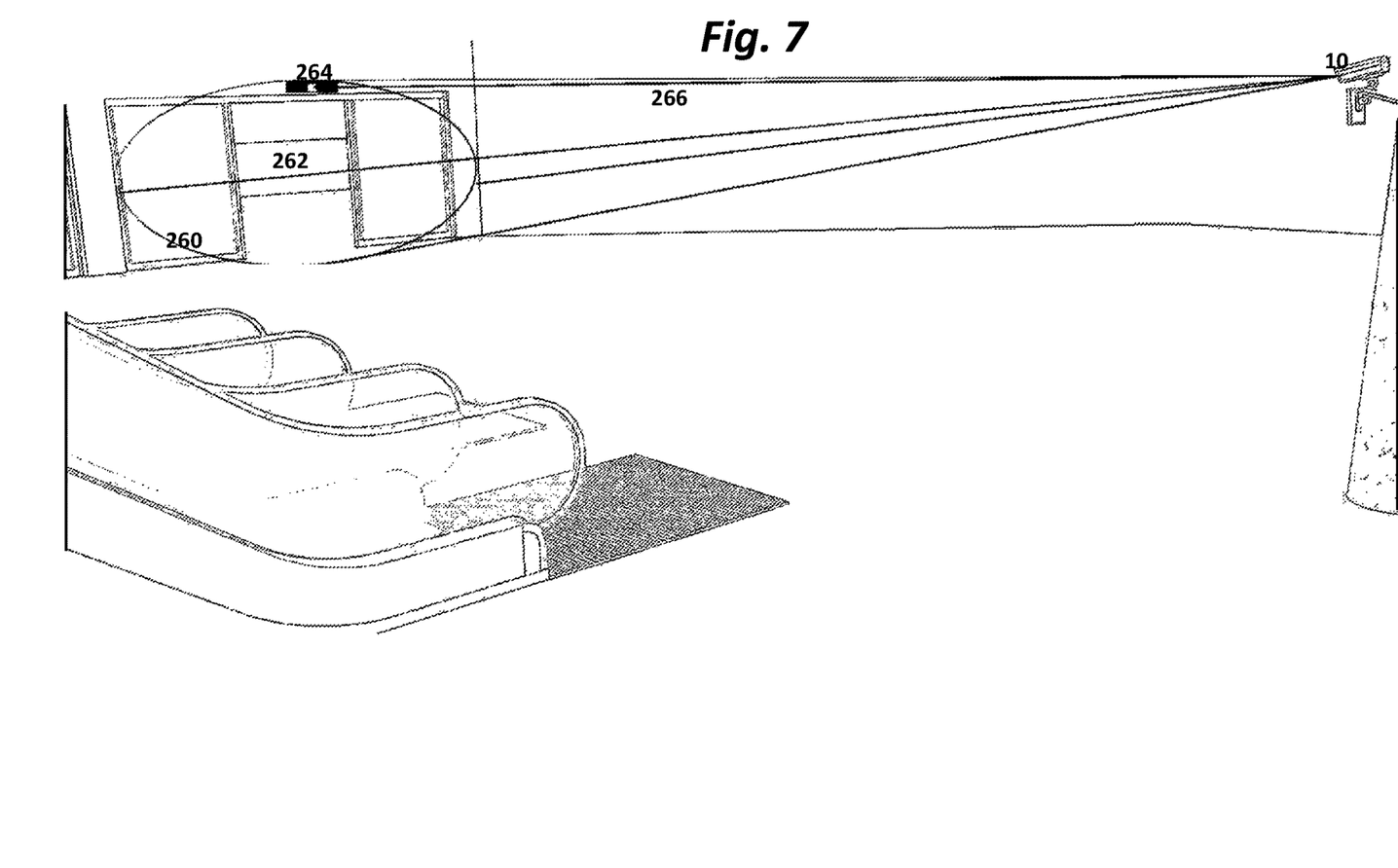
FIG. 7 illustrates an embodiment of the invention in a setting

FIG. 7 shows the previous core embodiment 10 of the system mounted such that its field of view 260 covers the entire entrance 262 to a mall or similar public space. By covering the entrance, the invention is assured that all people entering are seen by the system, and that they are effectively all facing towards the imaging system at some point during their passage through the volume covered by the field of view 260.

In addition, by mounting the system 10 on a column or wall at some distance from the entryway 262, the viewing angle is restricted to very shallow angles from zero to no more than fifteen degrees. It is well known that effective emissivity can vary significantly with viewing angles greater than 60 degrees, and to some degree below this; thus, limiting the imaging viewing angle is an important element of ensuring that the thermal measurements of the system are accurate.

To address environmental effects on the measurements, FIG. 7 shows a set of calibration and compensation sensors 264 which are set such that they are always within the field of view 260 of the cameras 14 and 18. Exactly what these sensors 264 are may vary. One possibility to maintain calibration is a known blackbody emitter whose temperature is very accurately maintained; this would provide the system 10 with a known comparison with which to adjust the sensed temperatures. A blackbody reference should ideally be kept to a temperature very similar to that of the targets (i.e., to some specific value around 98 degrees F.), as this is the range of real interest and the calibration and accuracy are most vital at that range.

Another option would be to include both accurate temperature and humidity sensors, which would allow the calculation of an atmospheric transmissivity coefficient. Another would be an infrared transmissometer, which is effectively a mirror mounted as shown to reflect a controlled infrared beam 266 back to its source, where the difference between the emitted and returned beam shows the transmission over the full path length. Any means which would allow the present invention to compensate for atmospheric transmission variation would be acceptable for the current invention.

An additional temperature sensor, or access to an existing temperature sensor, which measures the external temperature outside of the entryway may be required. Ideally, an entryway leading to the door 262 would be long enough to mitigate effects of external temperature, but where that is not possible, an external sensor will be necessary to understand what level of temperature compensation should be expected for persons just entering the area of the system.

Temperature is of course only one diagnostic criterion for detecting whether a person is ill; there are multiple others, some of which may also be detected by remote means. Previously, FIG. 1 showed the presence of an acoustic sensing array 22. Such an array may detect a target sound and then, using beamforming to determine an accurate bearing for the sound, provide a vector for the imaging system to use in determining the source of that sound; a steerable parabolic microphone may also allow for such localization. For illnesses, such diagnostics would include coughing, sneezing, particular breathing patterns, and breathing sounds such as wheezes and rales.

Figure 8:
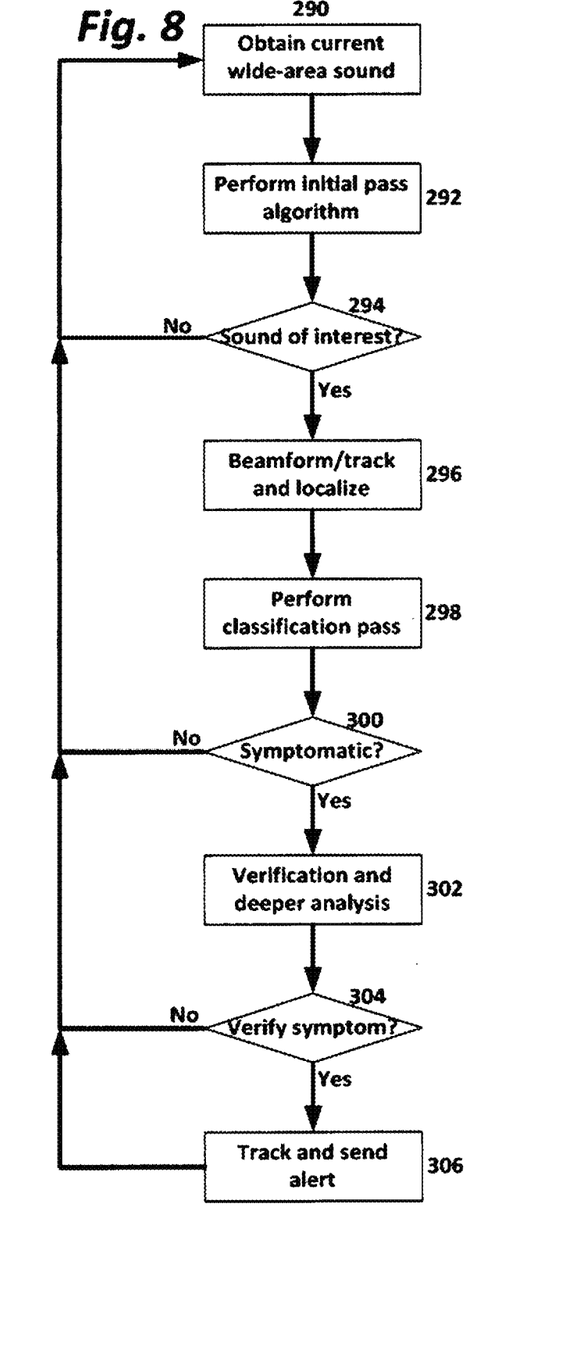
FIG. 8 shows a flowchart for acoustic detection of health-related anomalies

FIG. 8 shows a general flowchart for a system to perform the task of sound analysis. The system initially obtains the sounds 290 from the wider area of interest (roughly equal to the field of view of the cameras 14 and 18) and these are then processed and run through a first-pass algorithm 292 to detect sounds of potential interest. These would be filter or thresholding algorithms looking for some very basic characteristics—sound onset/rise and fall times, peaks, basic frequency range, etc. —to filter out most ordinary sounds but leave any that may be of specific interest. If no sounds of potential interest are found 294, the system returns to wide-area sound collection 290; if sounds of interest are found 294, the system then localizes the source 296 of the sound of interest and then performs a broad classification pass 298; this further refines the simple analysis of 292 and is intended to remove sounds that are effectively false positives—isolated ordinary coughs, sounds that turn out to be caused by something other than breathing-related activities, and so on—and begin the work of sorting the sound or sounds into general categories such as coughs or sneezes. If this second pass concludes 300 that there are no symptomatic sounds, it returns to the sound-gathering at 290. If it concludes 300 that there are likely symptomatic sounds present, the data is passed to a much more powerful analysis engine 302. This may include direct template comparisons, neural network or other deep-learning analysis of sounds, expert systems, or any other means of identifying medical-related sounds that may be known to those skilled in the art.

If the presence of a symptom is not verified 304 after analysis, the system returns to sound-gathering at 290; if a symptom or symptoms are verified, the subject is added to a direct tracking pool and an alert is sent 306.

Acoustic sensing has advantages in simplicity, convenience, and to an extent range, but the challenges of accurately sensing and localizing behavior such as coughs and breathing are considerable. Millimeter-wave sensors, such as those available from Texas Instruments, can perform millimeter-scale measurement over meter-scale distances; chest movement from breathing is well within the sensing range of such sensors. Coughing and similar behaviors involve distinctive body movements as well, of generally equal or greater magnitude. Research and testing has shown that even heartbeat can be detected by these sensors. An alternative embodiment is therefore described in connection with FIG. 9.

Figure 9:
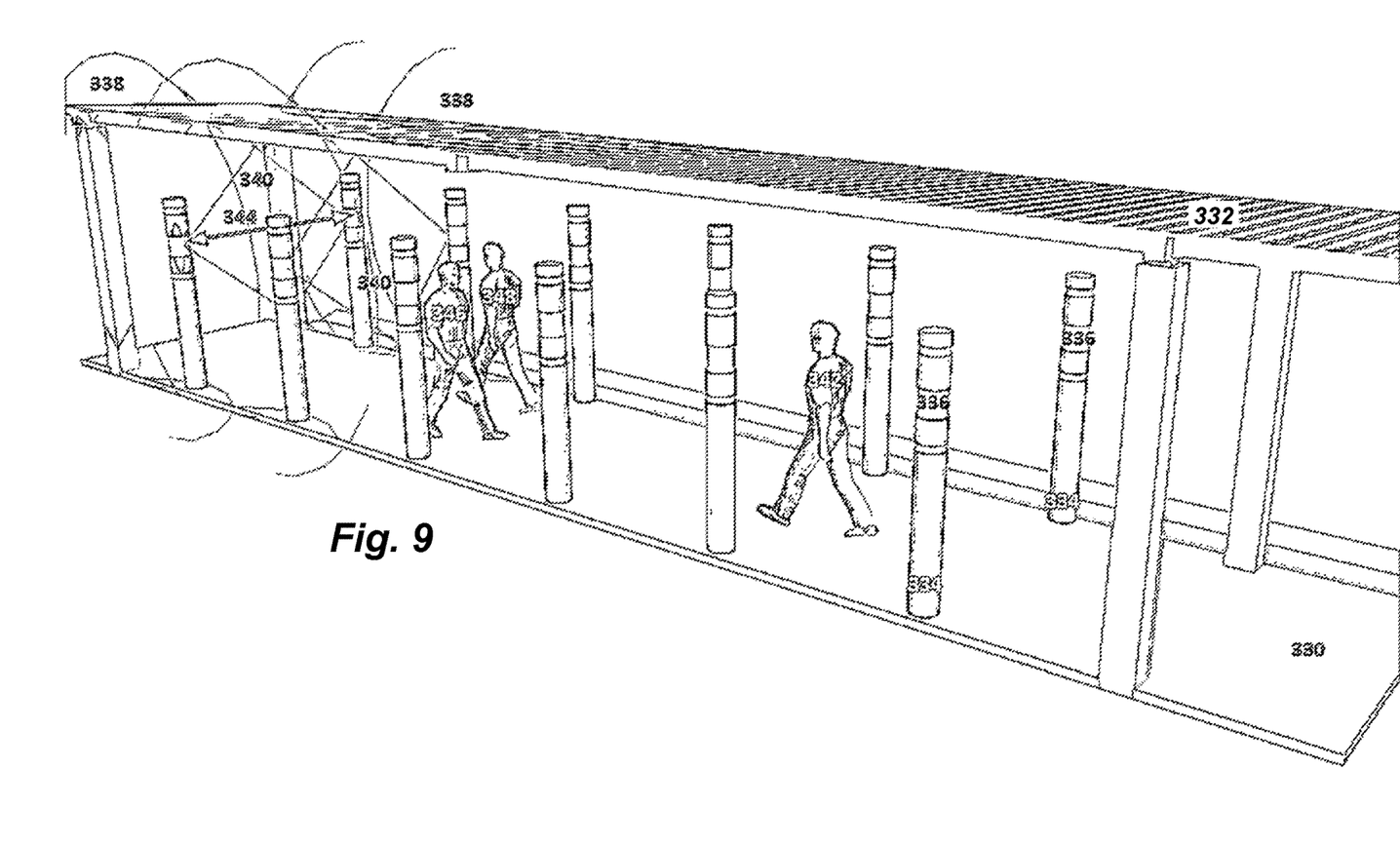
FIG. 9 illustrates a millimeter-wave sensing installation

In FIG. 9, a walkway 330 may be open or may have a covering 332; it may also be a completely enclosed hallway. In any event, poles or bollards 334 may be spaced along the walkway 330. These bollards 334 may incorporate millimeter-wave sensors 336; the sensors may be obvious or disguised as or accompanied by lighting or decoration that does not interfere with their function. Alternatively, the bollards may be replaced by gates such as those seen at airport security screening stations but longer in extent to cover a monitoring pathway.

In any event, the sensors 336 are designed to monitor a volume, in this case a conical volume 338, with an angle of view such that the overlap 340 in the center substantially encompasses the majority of any human subject 342 passing through it. The overlap 340 also extends side-to-side with a conical projection, ensuring that any human subject 342 remains in effective sensing area 338 of at least two bollard sensors 336 along the entire bollard 334-instrumented length of walkway 330.

This ensures that a continuous monitoring of a human subject 342 can be performed along that length. This is important as it allows the capture not of a single moment but of a significant period of time, during which there will be multiple breaths taken and many heartbeats to measure, and if the subject 342 is subject to frequent coughing, sneezing, or other involuntary events one or more of these may also be captured for analysis as a process rather than as a single sensed event.

Millimeter-wave sensors inherently measure all distances 344 across their sensing volume; thus, the bollard sensors 336 can track and construct millimeter-scale models/3-D images of the moving figures through the volume. In addition, even in a case when two persons 346 and 348 move through the same overall volume, the distance measurements 344 from two bollard sensors 336 allow the two individuals to be separately tracked and evaluated.

It should be understood that this is only one of many possible embodiments of this aspect of the invention, and in no way is the present invention restricted to this particular embodiment. The concept of using an archway like that of an airport security screening system has been mentioned. Another addition to the system could be to place additional sensors 336 on the roof of an enclosed walkway or hallway; this would improve the ability of the system to disambiguate between multiple people walking together, as with the base system shown in FIG. 9.

Figure 10:
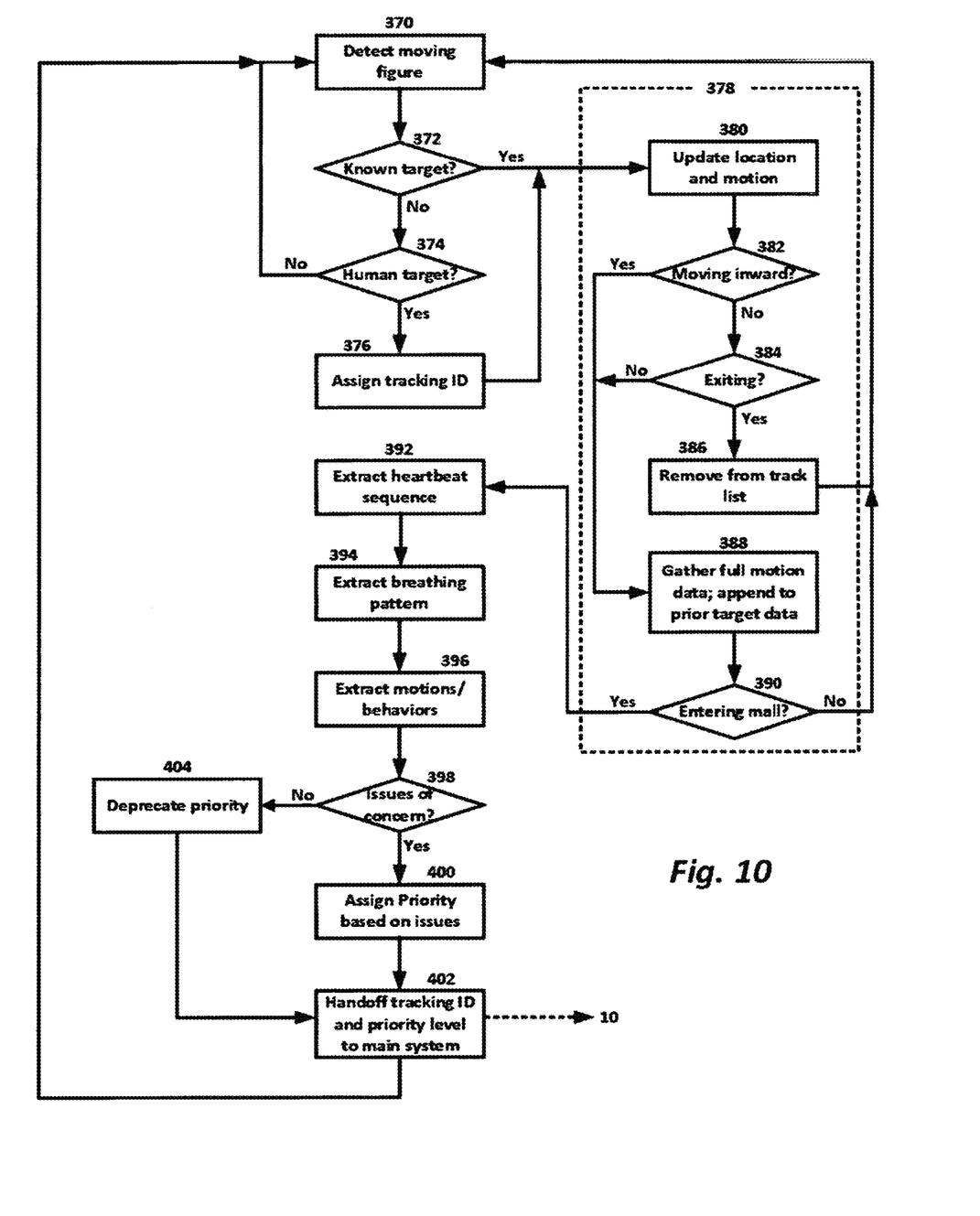
FIG. 10 shows a flowchart of the millimeter-wave sensing approach integrating with the prior imaging design FIG. 11 Illustrates a portable embodiment of the design It is noted that the drawings may not be to scale. The drawings are intended to depict only typical aspects of the invention, and therefore should not be considered as limiting

This subsystem embodiment of the invention may be a part of the larger whole; for example, it could form the walkway to the mall entrance 262 seen in FIG. 7, so that individuals could already be marked for tracking as they entered the camera field of view. FIG. 10 outlines a basic flowchart of operation for the system including the millimeter-wave sensing approach, assuming the main described system 10 is in-place in the interior of a mall, as shown in FIG. 7, and that the walkway as shown in FIG. 10 leads to the monitored entrance 262.

In FIG. 10, the sensors detect a moving FIG. 370. The instantaneous motion and location are compared to the known figures currently being tracked to determine if the figure is a known FIG. 372. If the figure is not known, it is examined to determine if it is a human FIG. 374. If it is not a human figure, the system returns to 370 and examines the next available detected figure. If the unknown target is a human figure, it is assigned a tracking ID 376 and sent to the tracking and data collection subsystem 378. If the figure is determined 372 to be a known figure, it is immediately sent to the tracking and data collection subsystem 378.

Subsystem 378 begins by updating the motion and location data for the assigned target ID. This is then evaluated for direction 382. If the target is not moving outward, the motion and location of the target are examined 384 to determine if the target is exiting the area of interest. If the target is exiting the area of interest, the ID is removed from the tracking list 386 and the system returns to 370. If the target is moving inward, or is not leaving the area of interest, the full motion data is gathered on the subject and appended 388 to the other data collected on that tracking ID. Motion and position data are then examined to determine 390 if the subject is entering the mall itself (through entrance 262 in FIG. 8); if not, the system returns to 370.

If the subject is entering the mall, this marks the ending of the ability to monitor the subject via millimeter wave; the maximum amount of data on the subject has been collected. To prevent potential issues of deliberate or innocent loitering on the system, a time cutoff may be assigned to a given subject, so that a constantly running "window" of data on the subject of no more than some determined number of seconds, minutes, etc. may be kept on the subject; this places a maximum ceiling on the amount of data storage and processing that may be demanded from the system during operation.

At this point, the system extracts the heartbeat record 392, the breathing pattern 394, and other significant motions/behaviors 396. These are all analyzed to determine if some, any, or all of these parameters show issues of concern 398. If there is an issue or issues present, the ID is assigned a higher priority 400 for observation based on those issues, which are made a part of the ID record. The tracking ID is then handed off 402 to the main system 10, and the millimeter wave subsystems returns to 370. If there are no issues present, the tracking ID priority is deprecated 404 and then handed off 402 to system 10 before returning to 370.

There are obvious challenges to determine the best specific methods to extract the data of interest; this includes sampling rate, extraction of the basic shape of the figure, segmenting the detected figure for the components (chest, head, arms, legs, etc.) of interest, and then locating the signals of interest within the noise of motion, movement of clothing, and so on. Most of these issues, and the solutions thereunto, are well-known to those skilled in the art.

The above has focused on a specific preferred embodiment of the invention. There are numerous alternative embodiments of the same invention.

Figure 11:
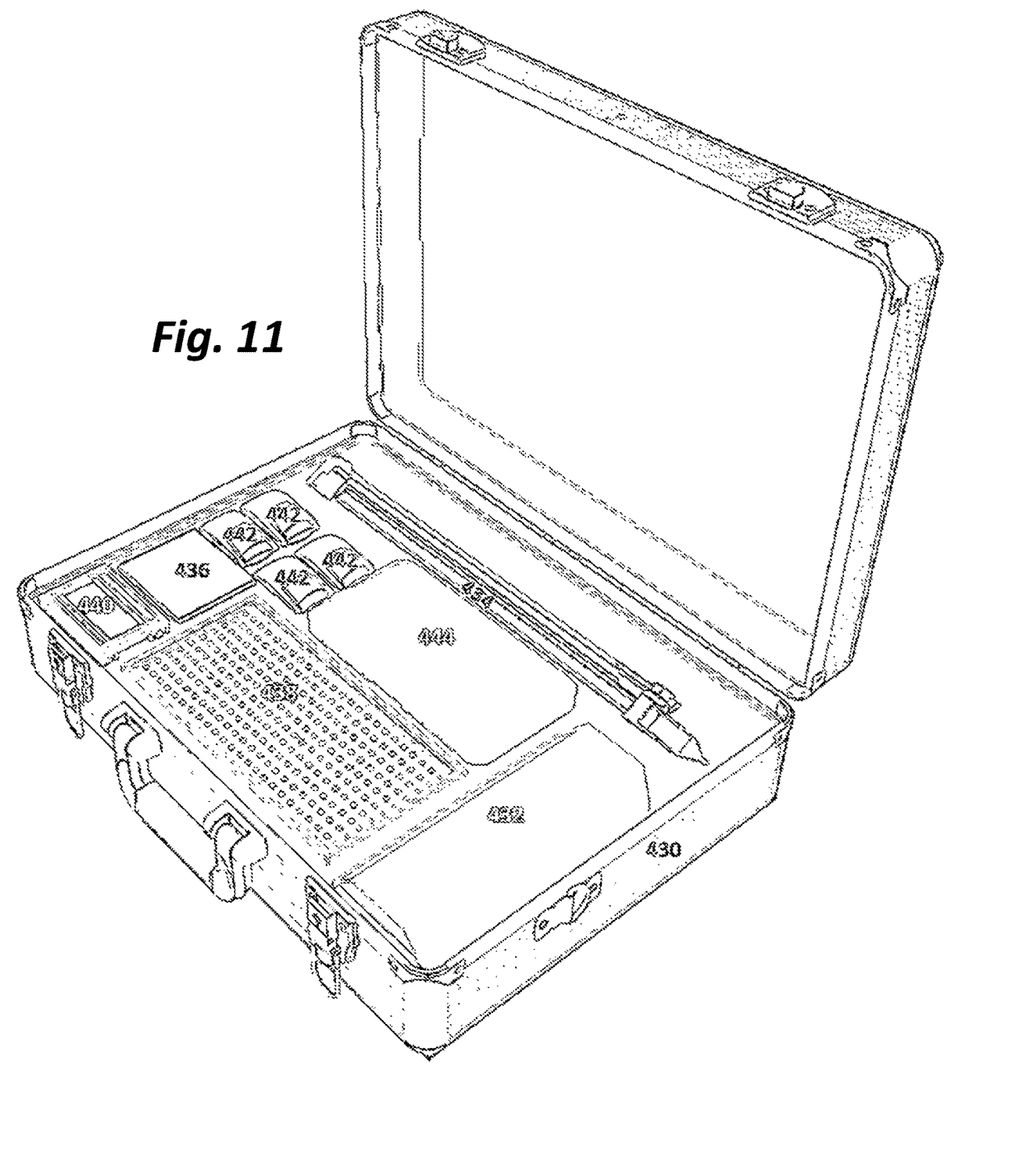

Portable system. The prior discussion was centered on systems that are inherently fixed-base (attached to a ceiling, integrated into a permanent bollard, etc.). This is not a necessary condition for the invention. A portable version of the system can be envisioned, as shown in FIG. 12. A protective case 430 transports the portable version of the system. The main sensing head 432, including versions of both cameras 14 and 18 and acoustic sensor 22 as well as processing power and communications links, is the central component of the portable system. A stable tripod 434, for areas where there is no suitable support available for the sensing head 432. The portable case 430 also includes a battery 436 and a foldable solar panel 438 to provide ongoing power to the system in areas where line power is unreliable or unavailable. A calibration and compensation sensor module 440 is included, which may incorporate a calibrated blackbody source, temperature sensors, humidity sensors, or others as may be appropriate. The portable system of FIG. 11 also includes four millimeter wave sensors 442. The case 444 includes mounting hardware, plugs for line power access, and other ancillary materials such as cables, assembly tools and so on. The main portable unit 432 may include a small display screen on the rear, or a separate display may be connected.

The foregoing description of various embodiments of this invention has been presented for purposes of illustration and description. It is not intended to be exhaustive or to limit the invention to the precise form disclosed and inherently many more modifications and variations are possible. All such modifications and variations that may be apparent to persons skilled in the art that are exposed to the concepts described herein or in the actual work product, are intended to be included within the scope of this invention disclosure.

What is claimed is:

1. A non-contact, non-intrusive, autonomous system for monitoring health conditions or parameters of persons in an area, said system comprising:
    a plurality of imaging devices including at least two imaging devices sensitive to radiation of distinct wavelength ranges, each with a particular field of view, wherein the fields of view of the at least two imaging devices are substantially co-registered at the area;
    a processor operatively connected to the imaging devices, the processor configured to autonomously monitor persons in the area by:
        receiving image data of the area acquired by the at least two imaging devices;
        identifying, for at least one person at least partially visible within the image data of the area acquired by each of the at least two imaging devices, facial image data corresponding to a face of the person, where the identifying includes extracting from the facial image data regions or elements of the image data that correspond to an area of interest on the face for the at least one person at least partially visible within the image data, where the extracting includes:
            identifying image data corresponding to a face of the at least one person from the image data of each of the at least two imaging devices; and
            identifying relevant components of the face in the facial image data of each of the at least two imaging devices;
        examining the identified facial image data for the at least one person acquired by each of the at least two imaging devices to determine at least one key parameter indicative of health, wherein the at least one key parameter indicative of health is determined from the facial image data of at least one of the relevant components of the face; and
        evaluating a need to send an alert in response to the determined at least one key parameter.

2. The system of claim 1, where the at least two cameras imaging devices includes at least one imaging device sensitive to infrared light.

3. The system of claim 2, where the at least one key parameter comprises a temperature of at least one of the relevant components of the face.

4. The system of claim 3, where the processor measures the temperature of the at least one of the relevant components of the face by compensating for at least one environmental variable.

5. The system of claim 3, where the processor measures the temperature of the at least one of the relevant components of the by detecting and compensating for surface variability of the face.

6. The system of claim 3, where the examining the at least one key parameter includes determining ranked priority of the relevant components of the face.

7. The system of claim 1, further comprising at least one acoustic sensor, where the processor further includes means to process acoustic data acquired by the at least one acoustic sensor.

8. The system of claim 7, where the acoustic data is processed to detect health-related signals.

9. The system of claim 8, where the processor further uses the health-related signals as at least one key parameter for evaluating the need to send the alert.

10. The system of claim 1, further comprising at least one target in the fields of view of the plurality of imaging devices that provides a reference for use in calibration or compensation.

11. The system of claim 10, where the at least one target includes a constant-temperature heat source for use in maintaining calibration in an infrared imaging device.

12. The system of claim 1, further comprising at least one millimeter wave sensor, where the processor further includes means to process millimeter wave data acquired by the at least one millimeter wave sensor.

13. The system of claim 12, where the at least one millimeter wave sensor cover a pathway of sufficient length to allow for acquiring multiple cycles of at least one relevant key physiological parameter.

14. The system of claim 13, where the processor further uses the at least one relevant key physiological parameters as at least one key parameter for evaluating the need to send the alert.

15. A non-contact, non-intrusive, autonomous method for determining medical health conditions or parameters of persons in an area, the method comprising at least one processor performing the following:

receiving sensor data from sensors that cover the area, wherein each sensor is a non-contact, non-intrusive sensor configured to acquire the corresponding sensor data;

extracting relevant data relating to at least one individual in the area from the sensor data, wherein the relevant data includes facial image data of the at least one individual;

adjusting the relevant data using at least one compensation process relevant to the relevant data;

determining a value of at least one health-related parameter for the at least one individual in the area using the adjusted relevant data;

assessing the value of the at least one health-related parameter to determine if the value of the at least one health-related parameter is outside of threshold limits; and generating an alert in response to determining the value of the at least one health-related parameter is outside of threshold limits.

16. The method of claim 15, where the facial image data includes image data acquired by sensors sensitive to radiation of a plurality of distinct wavelength ranges.

17. The method of claim 15, where the relevant data includes millimeter wave data acquired by at least one millimeter wave data acquisition sensor.

18. The method of claim 15, wherein the determining a value includes determining a temperature of the at least one individual using the facial image data and a ranked priority of a plurality of relevant components of the face.

19. The method of claim 15, where the adjusting includes extracting from the facial image data regions or elements of the facial image data that correspond to an area of interest on the face for the at least one individual.

20. The method of claim 19, where the extracting includes:
    identifying image data corresponding to a face of the at least one individual from the sensor data of each of at least two sensors; and
    identifying relevant components of the face in the facial image data of each of the at least two sensors.

* * * * *